United States Patent
Lee (10) Patent No.: US 10,799,381 B2
(45) Date of Patent: Oct. 13, 2020

(54) TENDON DEVICE FOR SUIT TYPE ROBOT FOR ASSISTING HUMAN WITH PHYSICAL STRENGTH

(71) Applicant: Daegu Gyeongbuk Institute of Science and Technology, Dalseong-gun, Daegu (KR)

(72) Inventor: Hee Don Lee, Gyeonggi-do (KR)

(73) Assignee: DAEGU GYEONGBUK INSTITUTE OF SCIENCE AND TECHNOLOGY, Techno jungang-daero, Hyeonpung-myeon, Dalseong-gun, Daegu (KR)

( * ) Notice: Subject to any disclaimer, the term of this patent is extended or adjusted under 35 U.S.C. 154(b) by 404 days.

(21) Appl. No.: 15/796,145

(22) Filed: Oct. 27, 2017

(65) Prior Publication Data
US 2018/0116851 A1    May 3, 2018

(30) Foreign Application Priority Data
Oct. 28, 2016    (KR) .......................... 10-2016-0141606

(51) Int. Cl.
*A61F 5/01*    (2006.01)
*G06F 3/01*    (2006.01)
(Continued)

(52) U.S. Cl.
CPC ............. *A61F 5/0102* (2013.01); *A61H 3/00* (2013.01); *G06F 3/016* (2013.01); *A61B 5/1071* (2013.01);
(Continued)

(58) Field of Classification Search
CPC ... A61H 3/00; A61H 1/00; A61H 1/02; A61H 1/023; A61H 1/0274; A61H 1/0277;
(Continued)

(56) References Cited

U.S. PATENT DOCUMENTS 1,669,931 A * 5/1928 Dowrie ..................... F16D 3/04
                                                    464/102
3,397,883 A * 8/1968 Kiehn .................. A61G 7/1017
                                                     482/67
(Continued)

FOREIGN PATENT DOCUMENTS

KR    100612031 B1    8/2006
KR    101324502 B1    11/2013

*Primary Examiner* — Quang D Thanh
(74) *Attorney, Agent, or Firm* — Olive Law Group, PLLC; Nathan P. Letts (57) ABSTRACT

A tendon device for a suit type robot which includes: a first wire and a second wire respectively fixed on a front portion and a rear portion of a joint of a user, and moving in a lengthwise direction thereof according to flexion-extension of the joint; a tendon driver including a first tendon module including a first pulley, and a second tendon module including a second pulley; a first pulley encoder measuring a rotary angle of the first pulley; a second pulley encoder for measuring a rotary angle of the second pulley; a controller configured to calculate tensions of the first wire and the second wire based on the rotary angle of the first and second pulleys in order to generate a control signal; and a driver configured to provide the first tendon module and the second tendon module with a driving power.

10 Claims, 5 Drawing Sheets

(51) Int. Cl.
*A61H 3/00* (2006.01)
*A61B 5/107* (2006.01)
*A61B 5/22* (2006.01)
*A61B 5/00* (2006.01)
*A61F 2/50* (2006.01)
*A61H 1/02* (2006.01)

(52) U.S. Cl.
CPC .............. *A61B 5/224* (2013.01); *A61B 5/4528* (2013.01); *A61F 2002/5093* (2013.01); *A61H 1/0259* (2013.01); *A61H 1/0262* (2013.01); *A61H 2201/1671* (2013.01); *A61H 2201/5007* (2013.01); *A61H 2201/5012* (2013.01); *A61H 2201/5061* (2013.01); *A61H 2201/5097* (2013.01)

(58) Field of Classification Search
CPC .............. A61H 1/0281; A61H 2203/05; A61H 2201/00; A61H 2201/0107; A61H 2201/0157; A61H 2201/1207; A61H 2201/1215; A61H 2201/16; A61H 2201/165; A61H 2201/164; A61H 2201/1642; A61H 2201/1657; A61H 2201/1664; A61H 2201/1671; A61H 2201/1678; A61H 2201/14; A61H 2201/1454; A61H 2201/1481; A61H 2201/5007; A61H 2201/5012; A61H 2201/5061; A61H 2201/5097; A61H 1/0259; A61H 1/0262; A61F 5/0102; A61F 2002/5093; G06F 3/016; A61B 5/1071; A61B 5/224; A61B 5/4258; A61B 5/112; A61B 5/0488; A61B 5/4528; B25J 9/00; B25J 9/0006; B25J 11/00; B25J 9/1045; B25J 9/126
See application file for complete search history.

(56) References Cited

U.S. PATENT DOCUMENTS

| | | | |
|---|---|---|---|
| 6,244,108 B1* | 6/2001 | McInnes | G01M 1/02 73/462 |
| 10,188,577 B2* | 1/2019 | Takenaka | A61H 3/00 |
| 2002/0026130 A1* | 2/2002 | West | A61F 5/0102 601/23 |
| 2006/0270951 A1* | 11/2006 | Ikeuchi | A61H 3/00 601/5 |
| 2015/0167798 A1* | 6/2015 | Gosselin | B25J 9/102 74/490.04 |
| 2015/0182366 A1* | 7/2015 | Takenaka | A61F 5/0123 602/16 |
| 2015/0190249 A1* | 7/2015 | Ishibashi | A61H 3/00 623/24 |
| 2015/0374573 A1* | 12/2015 | Horst | A61H 3/00 602/16 |
| 2016/0128890 A1* | 5/2016 | LaChappelle | A61H 1/024 623/30 |
| 2017/0027735 A1* | 2/2017 | Walsh | A61F 5/0102 |

* cited by examiner

TENDON DEVICE FOR SUIT TYPE ROBOT FOR ASSISTING HUMAN WITH PHYSICAL STRENGTH

CROSS-REFERENCE TO RELATED APPLICATION

This application claims the benefit of Korean Patent Application No. 10-2016-0141606, filed on Oct. 28, 2016, in the Korean Intellectual Property Office, the disclosure of which is incorporated herein in its entirety by reference.

BACKGROUND

1. Field

One or more embodiments relate to a suit type robot for assisting the old and the weak requiring physical strength assistance, patients who need to rehabilitate, and workers to which a large load is applied for a long period of time, with physical strength, and more particularly, to a tendon device for a suit type robot for assisting human with physical strength, wherein the suit type robot provides a tendon driver including a pair of tendon modules respectively using wires so that performance similar to those of muscles required in joint flexion-extension (agonistic muscle and antagonist muscle) may be performed by using tension of the wires and physical strength required in the joint movement may be assisted.

2. Description of the Related Art

Recently, an aging society has come, and thus, a ratio of population of senior citizens in social and economic aspects has been largely increasing, and demand for health management by using various devices and participation of elderly people in social activities has been increasing.

Also, in an industrial field, transfer equipment such as a forklift truck, a crane, etc. that transfers heavy materials instead of human beings is widely used, but the above equipment requires a relatively large moving space or installation space, and thus, usage range of the above equipment is very restricted.

Therefore, in a field where the above equipment is unable to be used, materials have to be transferred by human power, and this case, working efficiency degrades due to high working intensity and there is high risk of occurring industrial accidents.

Recently, research on wearable exoskeleton robots in the form of coupling a robot mechanism to a human body has been actively performed to address the above problems. Korean Registered Patent No. 10-1324502 discloses a wearable human power amplification device, and Korean Registered Patent No. 10-0612031 discloses a power assisting gait orthosis.

Besides the above technologies, a wearable human power amplification device according to the related art is a kind of exoskeleton robot wearable on a human being, and assists a wearer with a physical strength by recognizing a moving direction intended by the wearer based on a muscle stiffness sensor signal, a force sensor signal, a bio-signal, etc., and rotating a link corresponding to a skeleton by a set angle and a set speed by using a driving source such as a motor, a hydraulic cylinder, a pneumatic cylinder, etc.

In the wearable human power amplification device, a driving device such as a motor is provided adjacent to a joint portion or directly installed on the joint portion.

Figure 1A:
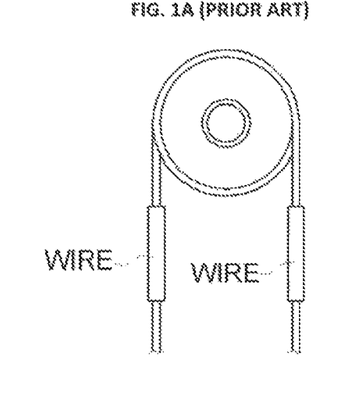
FIG. 1A (inset) and 1B are a diagram of an example of a tendon device for a suit type robot according to the prior art.
Figure 1B:
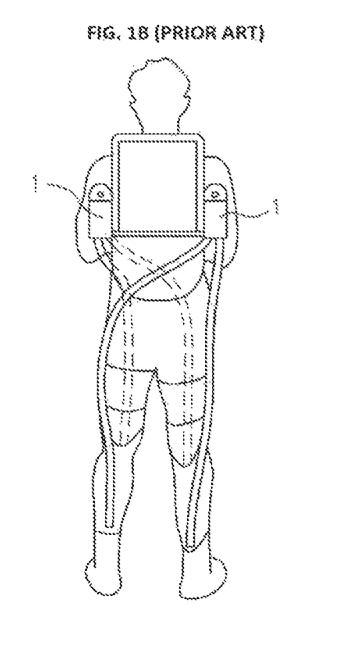

FIG. 1A-1B shows a suit type wearable robot according to the prior art, and the suit type wearable robot of the related art may be only used in a certain circumstance such as a level walking, but is unable to assist with the physical strength in such a case where flexion-extension of left and right joints simultaneously occur, e.g., sitting/standing-up, or flexion of a joint occurs during walking on stairs or slope.

In the suit type wearable robot according to the related art of FIG. 1A-1B, two wires for supporting power of joints that are symmetric with each other bilaterally in a human body are operated by one pulley in a driver 1, and thus, when one wire is pulled to a predetermined length by rotation of a motor, an opposite wire is unwound to the same length. However, when a person actually walks, flexion/extension angles of left and right joints in a human body do not correspond to each other.

Therefore, according to the driver 1 of the related art, a wire on a leg opposite to the other leg that is supported is loosened or the length of loosened wire is not sufficient, which may apply as a load to the joint in the human body. Thus, the driver 1 according to the related art is largely affected by walking posture of a wearer and a variation in sizes of human bodies.

Also, when the wearer continuously walks, physical strength assisting force supplied by the wire has to be transferred repeatedly to left and right sides, and a loosened wire causes delay in a time for transferring the force. In addition, if a force sensor for measuring a tension of the wire is attached, the measurement of the tension is not possible when the wire is loosened, and thus, there is limitation in controlling the wire.

SUMMARY

One or more exemplary embodiments include a tendon device for a suit type robot capable of assisting a wearer with a physical strength in every kind of movements during everyday life such as sitting, standing-up, walking on stairs and slope, as well as regular walking such as level walking, by providing a tendon driver including a pair of tendon modules each using a wire so as to support physical power to each joint in a human body through measuring of a tension of the wire and winding the wire.

Various aspects of the exemplary embodiments will be set forth in part in the description which follows and, in part, will be apparent from the description, or may be learned by practice of the presented embodiments.

According to an aspect of an exemplary embodiment, there is provided a tendon device for a suit type robot, the tendon device comprising: a first wire and a second wire respectively fixed on a front portion and a rear portion of a joint of a user, and moving in a lengthwise direction thereof according to flexion-extension of the joint; a tendon driver comprising a first tendon module including a first pulley on which the first wire is wound, and a second tendon module including a second pulley on which the second wire is wound; a first pulley encoder included in the first tendon module for measuring a rotary angle of the first pulley; a second pulley encoder included in the second tendon module for measuring a rotary angle of the second pulley; a controller configured to calculate tensions of the first wire and the second wire based on the rotary angle of the first pully measured by the first pulley encoder and the rotary angle of the second pulley measured by the second pulley encoder, in order to generate a control signal; and a driver configured to provide the first tendon module and the second tendon module with a driving power via a rotary shaft based on the control signal transferred from the controller.

The tendon device may further comprise a housing having an internal space, and a driving axis member crossing the internal space of the housing, the driving axis member coupled to the first tendon module and the second tendon module as penetrating therethrough, and connected to the rotary shaft of the driver so as to transfer the driving power to the first tendon module and the second tendon module from the driver.

The tendon device may further comprise: a first torsion spring provided at the first pulley and the driving axis member to generate torsion; and a second torsion spring provided at the second pulley and the driving axis member to generate torsion.

The first pulley and the second pulley each may include a coupling hole coupled to the driving axis member, a coupling piece may protrude from the coupling hole of each of the first pulley and the second pulley, a driving protrusion may protrude from an outer circumferential surface of the driving axis member in a direction perpendicular to an axial direction, one side of the first torsion spring may be fixed to the first pulley and the other side of the first torsion spring may be located between the coupling piece and the driving protrusion, and one side of the second torsion spring may be fixed to the second pulley and the other side of the second torsion spring may be located between the coupling piece and the driving protrusion.

The first tendon module may comprise: a first spur gear coupled to a side surface of the first pulley to rotate with rotation of the first pulley; and a first tension adjusting unit configured to adjust a tension of the first wire wound on the first pulley.

The second tendon module may comprise: a second spur gear coupled to a side surface of the second pulley to rotate with rotation of the second pulley; and a second tension adjusting unit configured to adjust a tension of the second wire wound on the second pulley.

The driver may comprise: a driving motor configured to selectively rotate the rotary shaft based on the control signal transferred from the controller; and a motor encoder provided at a side of the driving motor and configured to measure a rotating direction and a rotary angle of the rotary shaft.

According to an aspect of another exemplary embodiment, there is provided a tendon device for a suit type robot, the tendon device comprising: a first wire and a second wire respectively fixed on a front portion and a rear portion of a joint of a user, and moving in a lengthwise direction thereof according to flexion-extension of the joint; a tendon driver comprising a first tendon module including a first pulley on which the first wire is wound, and a second tendon module including a second pulley on which the second wire is wound; a controller configured to calculate tension of the first wire and the second wire based on a rotary angle of the first pulley and a rotary angle of the second pulley to generate a control signal; a driver configured to provide the first tendon module and the second tendon module with a driving power via a rotary shaft based on the control signal transferred from the controller; a driving axis member connected to the rotary shaft of the driver and configured to transfer the driving power to the first tendon module and the second tendon module from the driver; a first torsion spring provided at the first pulley and the driving axis member to generate torsion; and a second torsion spring provided at the second pulley and the driving axis member to generate torsion.

The first pulley and the second pulley each may include a coupling hole coupled to the driving axis member, a coupling piece may protrude from the coupling hole of each of the first pulley and the second pulley, a driving protrusion may protrude from an outer circumferential surface of the driving axis member in a direction perpendicular to an axial direction, one side of the first torsion spring may be fixed to the first pulley and the other side of the first torsion spring may be located between the coupling piece and the driving protrusion, and one side of the second torsion spring may be fixed to the second pulley and the other side of the second torsion spring may be located between the coupling piece and the driving protrusion.

The first tendon module may comprise: a first spur gear coupled to a side surface of the first pulley to rotate with rotation of the first pulley; and a first tension adjusting unit configured to adjust a tension of the first wire wound on the first pulley.

The second tendon module may comprise: a second spur gear coupled to a side surface of the second pulley to rotate with rotation of the second pulley; and a second tension adjusting unit configured to adjust a tension of the second wire wound on the second pulley.

The driver may comprise: a driving motor configured to selectively rotate the rotary shaft based on the control signal transferred from the controller; and a motor encoder provided at a side of the driving motor and configured to measure a rotating direction and a rotary angle of the rotary shaft.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Hereinafter, one or more embodiments of the present disclosure will be described in detail with reference to accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

Therefore, the description proposed herein is just a preferable example for the purpose of illustrations only, not intended to limit the scope of the disclosure, so it should be understood that other equivalents and modifications could be made thereto without departing from the spirit and scope of the disclosure.

The present disclosure relates to a suit type robot for assisting the old and the weak requiring physical strength assist, patients who need to rehabilitate, and workers to which a large load is applied for a long period of time, with physical strength, and more particularly, to a tendon device for a suit type robot for assisting human with physical strength, wherein the suit type robot provides a tendon driver including a pair of tendon modules respectively using wires so that performance similar to those of muscles required in joint flexion-extension (agonistic muscle and antagonist muscle) may be performed by using tension of the wires and physical strength required in the joint movement may be assisted, and the present disclosure will be described in detail below with reference to the accompanying drawings.

Figure 2A:
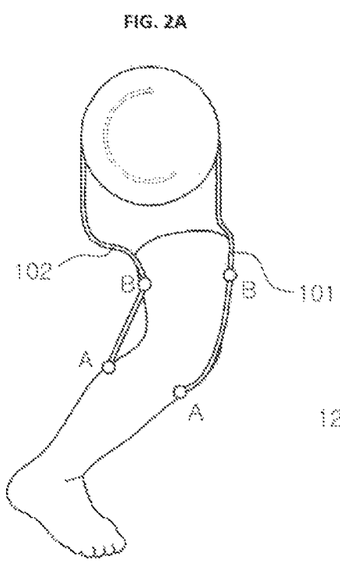
FIGS. 2A and 2B (inset) are a schematic diagram of an example of a tendon device for a suit type robot for assisting with a physical strength, according to an embodiment of the present disclosure.
Figure 2B:
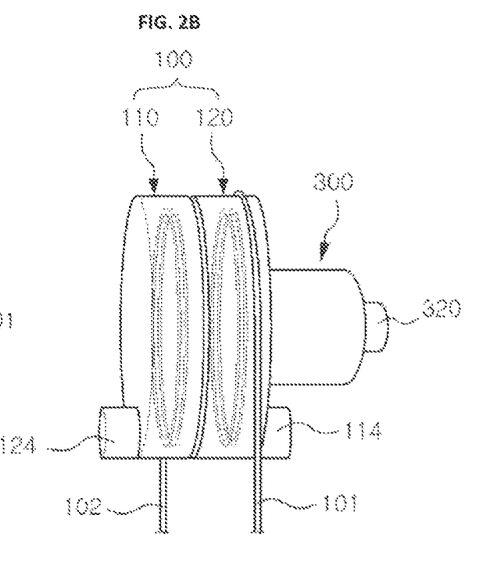
Figure 3:
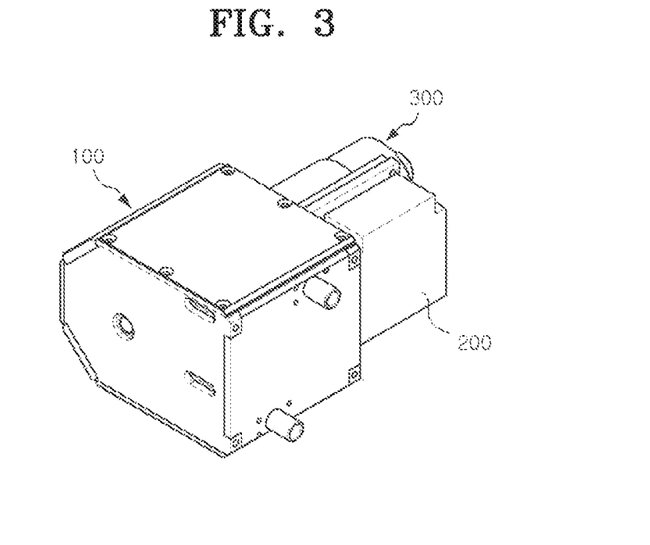
FIG. 3 is a diagram of an example of a tendon device for a suit type robot for assisting with a physical strength, according to an embodiment of the present disclosure.
Figure 4:
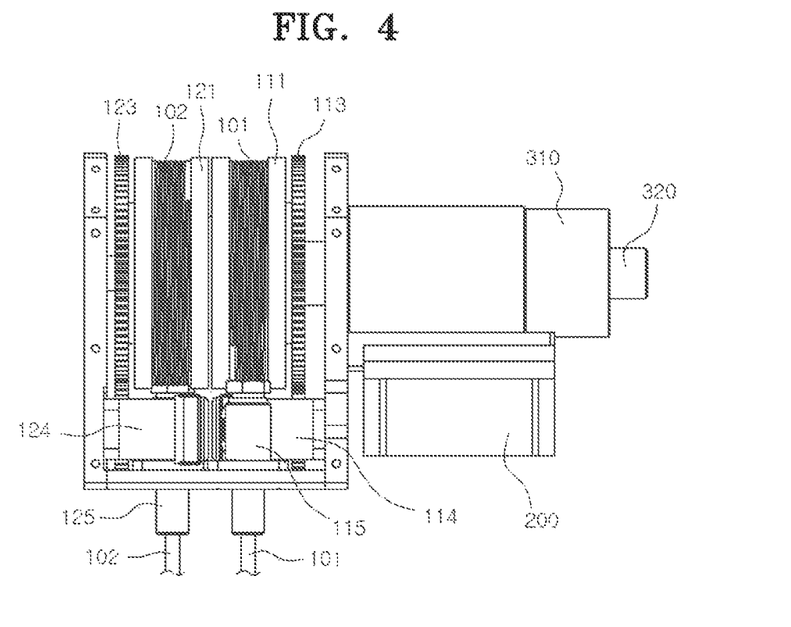
FIG. 4 is a side view of a tendon device according to an embodiment of the present disclosure.
Figure 5:
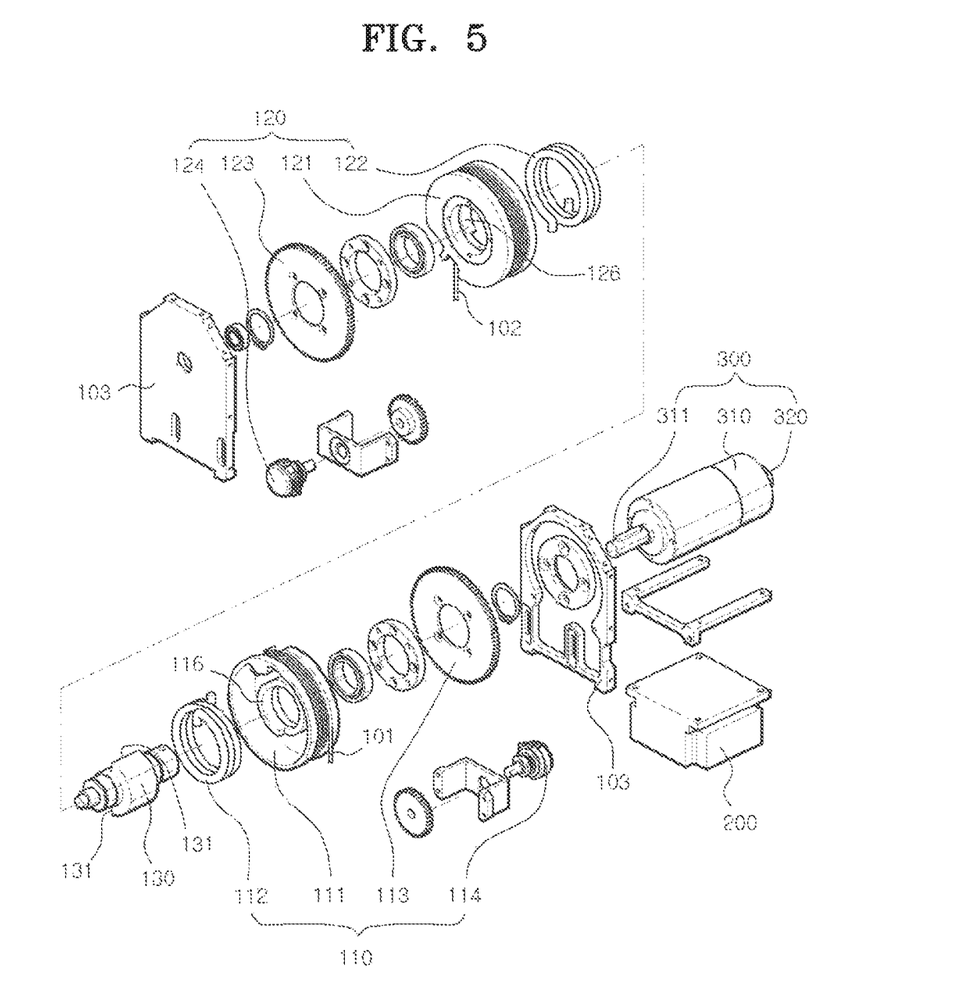
FIG. 5 is an exploded perspective view of a tendon device according to an embodiment of the present disclosure.
Figure 6:
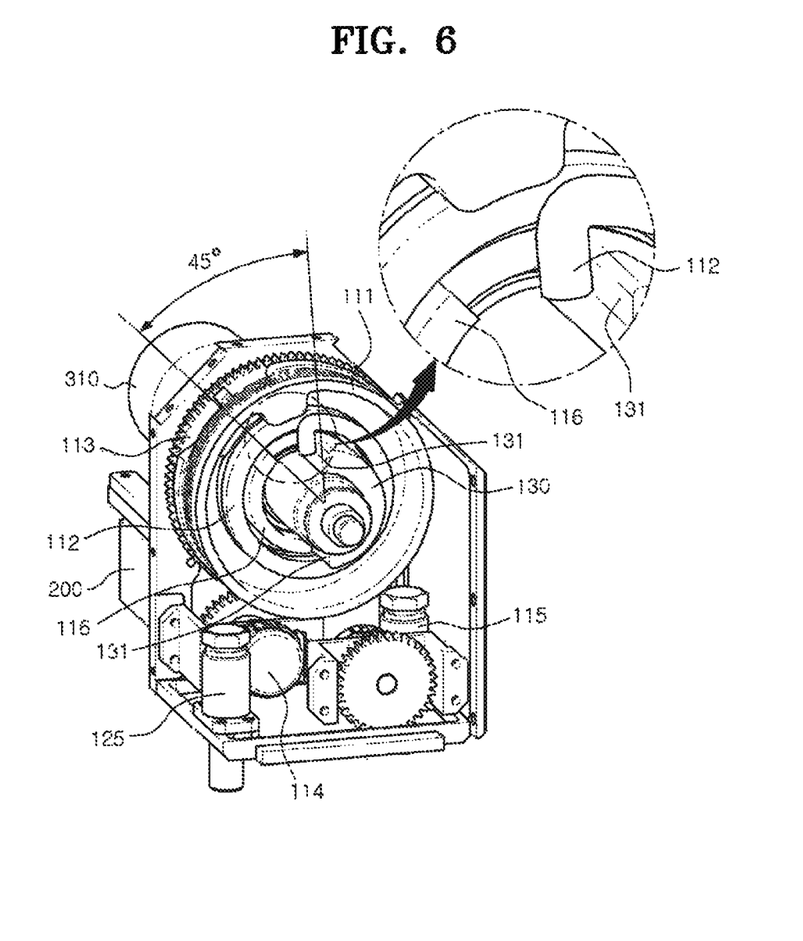
FIG. 6 is a diagram showing a partially cut tendon device according to an embodiment of the present disclosure.
Figure 7:
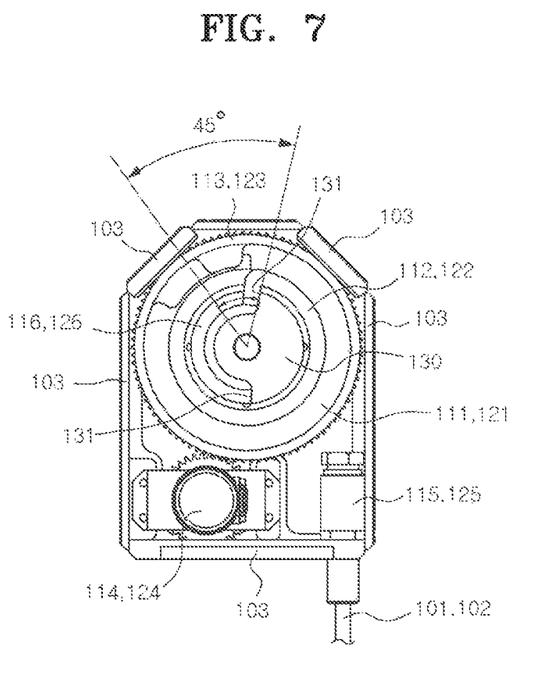
FIG. 7 is a diagram of an internal configuration of a tendon device according to an embodiment of the present disclosure.

Referring to FIGS. 2A-2B to FIG. 6, a tendon device for a suit type robot according to an embodiment of the present disclosure includes a first wire 101 and a second wire 102, a tendon driver 100, a controller 200, and a driver 300, wherein the first wire 101 and the second wire 102 are respectively fixed on a front portion and a rear portion of a joint of a user so as to move in a lengthwise direction thereof according to movement of the joint of the user (variation in a length of the wire unwound from a pulley).

Here, the first wire 101 and the second wire 102 are coated on an outer cover material including metal and a synthetic resin, and may be free to move in the lengthwise direction of the wire from inside of the outer cover material. This structure may not harm the skin of the user even when the wire moves.

Also, the first wire 101 and the second wire 102 copy functions of an agonistic muscle (muscle that leads bending and straightening motions of a joint) and an antagonist muscle (muscle that moves the joint in reverse direction in opposition to the agonistic muscle) used in the joint motion so as to support the physical strength, and thus, the user may sufficiently move the joint.

The first wire 101 and the second wire 102 are fixed around a joint, the physical strength of which is to be supported, in order to copy the agonistic muscle and the antagonist muscle. In the embodiment of the present disclosure, as shown in FIGS. 2A and 2B, the first wire 101 and the second wire 102 are provided on a knee joint from among lower limb joints of the user so as to assist the knee joint movement with the physical strength, and the first wire 101 between the first and second wires 101 and 102 is fixedly arranged on a front portion of the knee joint and the second wire 102 is fixedly arranged on a rear portion of the knee joint.

Here, lower ends of the first wire 101 and the second wire 102 are fixed around the knee joint, and both the first and second wires 101 and 102 have two attachment locations.

Here, the two attachment locations denote lower and upper portions of the knee joint. A lowest end of the wire, that is, a fixed point A, is located at a lower portion of the knee joint and a via point B through which the wire moves is located at an upper portion of the knee joint, so that the agonistic muscle and the antagonist muscle are copied by a variation in the length of the wire between the fixed point A and the via point B.

The wires may be fixed by a band that is detachable via a Velcro (not shown).

The first wire 101 and the second wire 102 are included in the tendon driver 100 in a state of being wound therein, and the tendon driver 100 includes a first tendon module 110 and a second tendon module 120 respectively winding upper ends of the first wire 101 and the second wire 102 therein in order to sense flexion-extension of the joint or to support the physical strength through the movements of the first wire 101 and the second wire 102.

Here, referring to FIGS. 4 to 7 illustrating the tendon driver 100 in more detail, the tendon driver 100 includes a housing 103 configuring a case, and a driving axis member 130 is provided in the housing 103 across an internal space of the housing 103.

Here, the driving axis member 130 includes driving protrusions 131 respectively protruding from upper and lower portions of an outer circumferential surface thereof to be perpendicular to an axial direction, and an end of the driving axis member 130 is coaxially connected to a rotary shaft 311 of the driver 300 so that the driving axis member 130 rotates with rotation of the rotary shaft 311.

Therefore, when the rotary shaft 311 rotates in a forward direction (clockwise direction) between the forward direction and a backward direction (counter-clockwise direction), the driving axis member 130 also rotates in the forward direction. Then, one of the driving protrusions 131 at the upper and lower portions on the outer circumferential surface of the driving axis member 130 to be perpendicular to the axial direction forces the pulleys of the first tendon module 110 and the second tendon module 120 to rotate.

In addition, in the internal space of the housing 103, the first tendon module 110 and the second tendon module 120, to which the driving axis member 130 is coupled penetrating through centers, unwind or wind the wires thereon according to a rotating direction of the driving axis member 130.

Here, the first tendon module 110 includes a first pulley 111, to which the driving axis member 130 is coupled through a center, having the first wire 101 wound thereon, and the first pulley 111 includes a first torsion spring 112. Thus, torsion is generated from the first torsion spring 112 according to the rotation of the first pulley 111, and thus, the rotation of the first pulley 111 is adjusted by the torsion so as to provide elasticity to the first wire 101 wound on the first pulley 111.

Here, the first torsion spring 112 is a coil spring type. When the first torsion spring 112 is coupled to inside of the first pulley 111, one side of the first torsion spring 112 is fixed in the first pulley 111 and the other side of the first torsion spring 112 is located within a torsion allowable space.

Here, the 'torsion allowable space' denotes a space in which the torsion of the first torsion spring 112 is applied (allowable range of spring deformation). The 'torsion allowable space' is generated when an arc-shaped coupling piece 116 protrudes along with a rim of a coupling hole of the first pulley 111 so that one of the driving protrusions 131 on the upper and lower portions of the driving axis member 130 and one end or the other end of the coupling piece 116 are spaced a predetermined distance apart from each other. The torsion allowable space is generated when the driving protrusion 131 and one end of the coupling piece 116 are spaced apart from each other at an angle of 45° with respect to each other based on a central axis of the driving axis member 130.

Therefore, the torsion allowable space allows the torsion of the first torsion spring 112 by an angle of 45° with respect to a direction in which tension of the first wire 101 is generated, and the driving axis member 130 is rotated in a direction opposite to the direction in which the tension of the first wire 101 is generated so that the first wire 101 is wound on the first pulley 111.

A first spur gear 113 is provided at a side surface of the first pulley 111, and the first spur gear 113 is rotated with the rotation of the first pulley 111. The first spur gear 113 is connected to a first pulley encoder 114 via a gear, and thus, the first pulley encoder 114 measures a rotary angle of the first pulley 111 in response to a rotary angle of the first spur gear 113.

The rotary angle of the first pulley 111 measured by the first pulley encoder 114 is output to the controller 200.

The first tendon module 110 includes a first tension adjusting unit 115, and the first tension adjusting unit 115 is coupled to a side surface of the housing 103 to adjust the tension of the first wire 101 wound on the first pulley 111 by using a frictional force.

In addition, the second tendon module 120 includes a second pulley 121, to which the driving axis member 130 is coupled through a center, having the second wire 102 wound thereon, and the second pulley 121 includes a second torsion spring 122. Thus, torsion is generated from the second torsion spring 122 according to the rotation of the second pulley 121, and thus, the rotation of the second pulley 121 is adjusted by the torsion so as to provide elasticity to the second wire 102 wound on the second pulley 121.

Here, the second torsion spring 122 is a coil spring type. When the second torsion spring 122 is coupled to inside of the second pulley 121, one side of the second torsion spring 122 is fixed in the second pulley 121 and the other side of the second torsion spring 122 is located within a torsion allowable space.

Here, the 'torsion allowable space' denotes a space in which the torsion of the torsion spring is applied (allowable range of spring deformation). The 'torsion allowable space' is generated when an arc-shaped coupling piece 126 protrudes along with a rim of a coupling hole of the second pulley 121 so that one of the driving protrusions 131 on the upper and lower portions of the driving axis member 130 and one end or the other end of the coupling piece 126 are spaced a predetermined distance apart from each other. The torsion allowable space is generated when the driving protrusion 131 and one end of the coupling piece 126 are spaced apart from each other at an angle of 45° with respect to each other based on a central axis of the driving axis member 130.

Therefore, the torsion allowable space allows the torsion of the second torsion spring 122 by an angle of 45° with respect to a direction in which tension of the second wire 102 is generated, and the driving axis member 130 is rotated in a direction opposite to the direction in which the tension of the second wire 102 is generated so that the second wire 102 is wound on the second pulley 121.

According to the present embodiment, the first pulley 111 is elastically connected to the driving axis member 130 via the first torsion spring 112, and the second pulley 121 is elastically connected to the driving axis member 130 via the second torsion spring 122. Thus, influence of the rotation of the first pulley 111 and the rotation of the second pulley 121 on each other may be reduced. For example, when the driving axis member 130 rotates, the rotation of the first pulley 111 and the second pulley 121 is affected, but when the first pulley 111 only rotates in a state where the driving axis member 130 stops rotating, the influence of the rotation of the first pulley 111 on the second pulley 121 may be reduced due to the first torsion spring 112.

A second spur gear 123 is provided at a side surface of the second pulley 121, and the second spur gear 123 is rotated with the rotation of the second pulley 121. The second spur gear 123 is connected to a second pulley encoder 124 via a gear, and thus, the second pulley encoder 124 measures a rotary angle of the second pulley 121 in response to a rotary angle of the second spur gear 123.

The rotary angle of the second pulley 121 measured by the second pulley encoder 124 is output to the controller 200.

The second tendon module 120 includes a second tension adjusting unit 125, and the second tension adjusting unit 125 is provided at a side surface of the housing 103 to adjust the tension of the second wire 102 wound on the second pulley 121 by using a frictional force.

The first tendon module 110 and the second tendon module 120 of the tendon driver 100 are electrically connected to the controller 200, and the controller 200 is electrically connected to the first pulley encoder 114 and the second pulley encoder 124 so as to generate and output a control signal according to flexion-extension of a joint based on measurement values sensed by the first pulley encoder 114 and the second pulley encoder 124.

That is, the first and second pulleys 111 and 121 rotate due to the movement of the first and second wires 101 and 102, and the first pulley encoder 114 and the second pulley encoder 124 measure the rotary angles of the first and second pulleys 111 and 121 to determine the flexion-extension of the joint, and then, the control signal is generated and output according to the determination.

Therefore, the first pulley encoder 114 and the second pulley encoder 124 included respectively in the first tendon module 110 and the second tendon module 120 of the tendon driver 100 respectively measure the rotary angles of the first and second pulleys 111 and 121. The controller 200 calculates displacement amounts of the first and second torsion springs 112 and 122 based on the measured rotary angles of the first and second pulleys 111 and 121, and calculates tensions of the first wire 101 and the second wire 102 based on the displacement amounts of the first and second torsion springs 112 and 122.

The controller 200 operates using the tensions of the first wire 101 and the second wire 102 to generate a control signal suitable for the calculated tensions and transfer the control signal to the driver 300.

The control signal generated by the controller 200 is transferred to the driver 300. Since the driver 300 is electrically connected to the controller 200 and is axially connected to the tendon driver 100, the driver 300 provides the first tendon module 110 and the second tendon module 120 with a driving power via the rotary shaft 311 based on the control signal output from the controller 200.

When one of the first pulley 111 and the second pulley 121 is rotated by the control signal transferred to the first tendon module 110 and the second tendon module 120, one of the first wire 101 and the second wire 102 is wound again, and then, the physical strength of the agonistic muscle of the joint movement is assisted by a pulling force.

Here, the driver 300 includes a driving motor 310 that selectively rotates the rotary shaft 311 based on the control signal output from the controller 200, and a motor encoder 320 is provided at a side of the driving motor 310 to measure a rotating direction and a rotary angle of the rotary shaft 311 of the driving motor 310 and output the measurement value to the controller 200.

Therefore, in the tendon device for the suit type robot according to the embodiment of the present disclosure, the first and second wires 101 and 102 from the tendon driver are attached to a human body in order to assist the flexion-extension operation of the joint with the physical strength, and the first and second wires 101 and 102 respectively perform functions of an agonistic muscle and an antagonist muscle during the flexion-extension movements.

Here, during the flexion of the knee joint, the second wire 102 functions as the agonistic muscle and the first wire 101 functions as the antagonist muscle, and during the extension of the knee joint, the first wire 101 functions as the agonistic muscle and the second wire 102 functions as the antagonist muscle.

In addition, since the first wire 101 and the second wire 102 are attached at different locations of the human body, a variation amount (length of the wire unwound from the pulley) of movement of the wire functioning as the agonistic muscle and a variation amount (length of the wire unwound from the pulley) of movement of the wire functioning as the antagonist muscle during the flexion/extension movements are different from each other, and a difference between the variations in the two wires 101 and 102 due to the joint movements is compensated for by the displacement amounts of the first and second torsion springs 112 and 122 respectively included in the first and second pulleys 111 and 121.

The first and second pulleys 111 and 121 only allow the deformation of the spring (torsion allowable space) to a certain angle in a direction in which the tension of the wires is generated by using the coupling pieces 116 therein, and thus, the two wires 101 and 102 operate independently from each other.

Also, the first and second pulleys 111 and 121 included in the tendon driver 100 respectively use the first and second torsion springs 112 and 122 to apply elasticity to the wires and to ensure safety even in a wrong operation of the suit type robot. In addition, rotating elasticity is applied to the first and second pulleys 111 and 121 of the first and second tendon modules 110 and 120 through the first and second torsion springs 112 and 122, and thus, safety of a wearer may be improved and reverse-mobility may be improved and interactivity between the human being and robot may be measured during controlling the joint movement. Thus, the joint movement may be precisely controlled.

Moreover, the two wires maintain constant tensions during the flexion/extension of the joints of the human body, and thus, the force may be rapidly transferred when changing the flexion/extension states.

In addition, the rotations of the first and second pulleys 111 and 121 due to the deformation of the first and second torsion springs 112 and 122 are measured by using encoders, and relative rotary angles are measured by using gears in order to improve accuracy. The tension of the wire may be measured based on the measured rotary angles of the first and second pulleys 111 and 121 and a spring constant calculated in a design stage, and the interactivity between the human being and the robot may be calculated by the measured tensions of wires and the calculated interactivity used to control the physical strength assistance of the suit type robot.

The tendon device for the suit type robot for assisting human with physical strength according to the embodiment of the present disclosure is capable of assisting a wearer with a physical strength in every kind of movements during everyday life such as sitting, standing-up, walking on stairs and slope, as well as regular walking such as level walking, by providing a tendon driver including a pair of tendon modules each using a wire so as to support physical power to each joint in a human body through measuring of a tension of the wire and winding the wire.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

What is claimed is:

1. A tendon device for a wearable suit robot, the tendon device comprising:
    a first wire and a second wire respectively adapted to be fixed on a front portion and a rear portion of a joint of a user, and varying in length thereof according to flexion-extension of the joint;
    a tendon driver comprising a first tendon module including a first pulley on which the first wire is wound, and a second tendon module including a second pulley on which the second wire is wound;
    a first pulley encoder included in the first tendon module for measuring a rotary angle of the first pulley;
    a second pulley encoder included in the second tendon module for measuring a rotary angle of the second pulley;
    a controller configured to calculate tensions of the first wire and the second wire based on the rotary angle of the first pulley measured by the first pulley encoder and the rotary angle of the second pulley measured by the second pulley encoder, in order to generate a control signal;
    a driver configured to provide the first tendon module and the second tendon module with a driving power via a rotary shaft based on the control signal transferred from the controller;
    a housing having an internal space;
    a driving axis member crossing the internal space of the housing, the driving axis member coaxially coupled to the first tendon module and the second tendon module as penetrating therethrough, and wherein the driving axis member is connected to the rotary shaft of the driver and configured to transfer the driving power to the first tendon module and the second tendon module from the driver;
    a first torsion spring provided at the first pulley and the driving axis member to generate torsion; and
    a second torsion spring provided at the second pulley and the driving axis member to generate torsion.

2. The tendon device of claim 1, wherein the first pulley and the second pulley each includes a coupling hole coupled to the driving axis member, wherein a coupling piece protrudes from the coupling hole of each of the first pulley and the second pulley,
    a driving protrusion protrudes from an outer circumferential surface of the driving axis member in a direction perpendicular to an axial direction,
    one side of the first torsion spring is fixed to the first pulley and an other side of the first torsion spring is located between the coupling piece and the driving protrusion, and
    one side of the second torsion spring is fixed to the second pulley and an other side of the second torsion spring is located between the coupling piece and the driving protrusion.

3. The tendon device of claim 1, wherein the first tendon module comprises:

a first spur gear coupled to a side surface of the first pulley to rotate with rotation of the first pulley; and a first tension adjusting unit to adjust a tension of the first wire wound on the first pulley.

4. The tendon device of claim 3, wherein the second tendon module comprises:

a second spur gear coupled to a side surface of the second pulley to rotate with rotation of the second pulley; and a second tension adjusting unit to adjust a tension of the second wire wound on the second pulley.

5. The tendon device of claim 1, wherein the driver comprises:

a driving motor configured to selectively rotate the rotary shaft based on the control signal transferred from the controller; and a motor encoder provided at a side of the driving motor and configured to measure a rotating direction and a rotary angle of the rotary shaft.

6. A tendon device for a wearable suit robot, the tendon device comprising:

a first wire and a second wire respectively adapted to be fixed on a front portion and a rear portion of a joint of a user and varying in length thereof according to flexion-extension of the joint;

a tendon driver comprising a first tendon module including a first pulley on which the first wire is wound, and a second tendon module including a second pulley on which the second wire is wound;

a controller configured to calculate tension of the first wire and the second wire based on a rotary angle of the first pulley and a rotary angle of the second pulley to generate a control signal;

a driver configured to provide the first tendon module and the second tendon module with a driving power via a rotary shaft based on the control signal transferred from the controller;

a driving axis member coaxially connected to the rotary shaft of the driver and configured to transfer the driving power to the first tendon module and the second tendon module from the driver;

a first torsion spring provided at the first pulley and the driving axis member to generate torsion; and a second torsion spring provided at the second pulley and the driving axis member to generate torsion.

7. The tendon device of claim 6, wherein the first pulley and the second pulley each includes a coupling hole coupled to the driving axis member, wherein a coupling piece protrudes from the coupling hole of each of the first pulley and the second pulley, a driving protrusion protrudes from an outer circumferential surface of the driving axis member in a direction perpendicular to an axial direction, one side of the first torsion spring is fixed to the first pulley and an other side of the first torsion spring is located between the coupling piece and the driving protrusion, and one side of the second torsion spring is fixed to the second pulley and an other side of the second torsion spring is located between the coupling piece and the driving protrusion.

8. The tendon device of claim 6, wherein the first tendon module comprises:

a first spur gear coupled to a side surface of the first pulley to rotate with rotation of the first pulley; and a first tension adjusting unit to adjust a tension of the first wire wound on the first pulley.

9. The tendon device of claim 8, wherein the second tendon module comprises:

a second spur gear coupled to a side surface of the second pulley to rotate with rotation of the second pulley; and a second tension adjusting unit configured to adjust a tension of the second wire wound on the second pulley.

10. The tendon device of claim 6, wherein the driver comprises:

a driving motor configured to selectively rotate the rotary shaft based on the control signal transferred from the controller; and a motor encoder provided at a side of the driving motor and configured to measure a rotating direction and a rotary angle of the rotary shaft.

* * * * *